United States Patent [19]

Ingbar

[11] Patent Number: 4,472,508
[45] Date of Patent: Sep. 18, 1984

[54] TEST FOR DETECTING AND MEASURING THE GRAVES' DISEASE-SPECIFIC IMMUNOGLOBULINS

[75] Inventor: Sidney H. Ingbar, Brookline, Mass.

[73] Assignee: The Beth Israel Hospital Association, Boston, Mass.

[21] Appl. No.: 454,717

[22] Filed: Dec. 30, 1982

[51] Int. Cl.$^3$ .................... G01N 33/58; G01N 33/60; G01T 1/00

[52] U.S. Cl. .................................. 436/500; 436/503; 436/504; 436/506; 436/512; 436/529; 436/804; 436/811; 436/825

[58] Field of Search ............... 436/500, 503, 504, 506, 436/512, 529, 804, 811, 825

[56] References Cited

PUBLICATIONS

Teng et al., Clin. Endocrinol., 6, (1977), 207–211.
DeBruin et al., ACTA Endocrinologica, 100, (1982), 245–251.
DeBruin et al., ACTA Endocrinologica, 102, (1983), 49–56.
Valente et al., Proc. Natl. Acad. Sci. U.S.A., 79, (1982), 6680–6684.
Yavin et al., Proc. Natl. Acad. Sci. U.S.A., 78, (1981), 3180–3184.
Kotulla, Aulbert, Meinhold, Adlkofer, Wenzel, Schleusener, Kruck, Kruck, "Methodological Approaches to Measuring Thyroid Stimulating Factors with a Radioligand Receptor Assay," Freie Universität.
Bernard Rees Smith, Reginald Hall: "Thyroid-Stimulating Immunoglobulins in Graves' Disease," The Lancet, Aug. 24, 1974.
S. Quasim Mehdi, Joseph P. Kriss: "Preparation of Radiolabeled (TSI) by Recombining TSI Heavy Chains with $^{125}$I-Labeled Light Chains: Direct Evidence that the Product Binds to the Membrane Thyrotropin Receptor and Stimulates Adenulate Cyclase," Endocrinology, vol. 103, #1, (1978).
Yukio Ochi, Shiro Hosoda, Takashi Hachiya, Manabu Yoshimura, Tadayoshi Miyazaki, Yoshihiro Kajita, "Studies on a Receptor Assay for an Antibody to Human Thyroid Plasma Membrane," ACTA Endocrinologica, (1979).
Michizo Kishihara, Yoshinobu Nakao, Yasuto Baba, Shigeru Matsukura, Kanji Kuma, Takuo Fujita, "Interaction between Thyroid-Stimulating Immunoglobulins and Thyrotropin Receptors in Fat Cell Membranes," Journal of Clinical Endocrinology and Metabolism, vol. 49, (1979).
Junji Konishi, Yasuhiro Iida, Kanji Kasagi, Katsuji Ikekubo, Kanji Kuma, Kanji Torizuka, "Adipocyte-TSH-Receptor-related Antibodies in Graves' Disease Detected by Immunoprecipitation," Endocrinology, Japan, vol. 29, (1982).
Tien-Wen Tao, Joseph P. Kriss, "Membrane-Binding Antibodies in Patients with Graves' Disease and other Anteimmune Diseases," Journal of Clinical Endocrinology and Metabolism, vol. 55, (1982).
Beall, Chopra, Solomon, Kruger, "Serum Protein Inhibition of Thyrotropin Binding to Human Thyroid Tissue," Journal of Clinical Endocrinology and Metabolism, vol. 47, (1978).
Fenzi, Macchia, Bartalena, Mazzanti, Baschieri, DeGroot, "Radio-receptor Assay of TSH: Its Use to Detect Thyroid-Stimulating Immunoglobulins," J. Endocrinol. Invest., 1:17, (1978).
Endo, Amir, Ingbar, "Development and Evaluation of a Method for the Partial Purification of Immunoglobulins Specific for Graves' Disease," J. of Clinical Endocrinol. & Metab., vol. 52, (1981).
Bliddal, "A Stable, Reproducible Radioreceptor Assay for Thyrotropin Binding Inhibiting Immunoglobulins (TBII)," Scand. J. Clin. Lab. Invest., vol. 41, 441–449, (1981).

(List continued on next page.)

*Primary Examiner*—Christine M. Nucker
*Attorney, Agent, or Firm*—Kenway & Jenney

[57] ABSTRACT

An immunoassay for a specific antibody, particularly Graves' disease-specific antibody, in which interfering reactions by the reactive ends of similar antibodies are eliminated by the step of occluding the interfering reactive ends with an antibody against the interfering reactive ends.

13 Claims, 7 Drawing Figures

PUBLICATIONS

Biro, "Thyroid-Stimulating Antibodies in Graves' Disease and the Effect of Thyrotrophin-Binding Globulins on Their Determination," J. of Endocrinology, vol. 92, pp. 175–184, (1982).

Navarro, Gomez, Pastor, Soler, "Antibodies Against TSH Receptor in Graves' Disease: Relation Between cGMP/cAMP Release," B.7. Hormone Receptors, pp. 575–578.

Navarro, Gomez, Pastor, Soler, "Antibodies Against TSH Receptor in Graves' Disease: Evaluation by Release of cAMP," B.7. Hormone Receptors, pp. 571–574.

Shishiba, Ozawa, Ohtsuki, Shimuzu, "Discrepancy between Thyroid-Stimulating and Thyrotropin-Binding Inhibitory Activities of Graves' Immunoglobulin Gs Assessed in the Mouse," J. of Clinical Endocrinology and Metabolism, vol. 54, pp. 858–862, (1982).

Kishihara, Nakao, Baba, Kobayashi, Matsukura, Kuma, Fujita, "Interaction between Thyrotropin (TSH) Binding Inhibitor Immunoglobulins (TBII) and Soluble TSH Receptors in Fat Cells," J. of Clin. Endocrinology & Metabolism, vol. 52, p. 665, (1981).

Sato, Zakarija, McKenzie, "Influence of Normal Human IgG and of TSAb on the Binding of Thyrotropin to Thyroid Plasma Membranes," Endocrine Research Con. 5(4), 259–269, (1978).

Mehdi, "Evidence that Human Thyroid Stimulating Immunoglobulins-G of Graves' Disease are Antibodies to Human Thyroid Cell-Surface Antigens," Oxford Univ.

TEST FOR DETECTING AND MEASURING THE GRAVES' DISEASE-SPECIFIC IMMUNOGLOBULINS

BACKGROUND OF THE INVENTION

The present invention relates to an immunoassay and more particularly to an immunoassay for antibodies specific to Graves' disease.

Graves' disease is a disorder characterized by several abnormalities, the most common and important of which is enlargement of the thyroid (goiter) and overproduction of thyroid hormones (hyperthyroidism). Graves' disease is one of three diseases classified as autoimmune thyroid diseases, the others being chronic lymphocytic thyroiditis (Hashimoto's disease) and primary myxedema (primary thyroid failure). Among the reasons these diseases are grouped together as autoimmune thyroid diseases is that the serum of patients with these disorders usually contain, in varying titer, antibodies against a variety of antigens present in the thyroid cell, particularly on the cell membrane.

Thyroid function is normally regulated by a peptide hormone, thyroid-stimulating hormone (TSH), secreted by the pituitary gland. The first and requisite step in the action of TSH on the thyroid gland is its binding to particular regions of the thyroid cell membrane that have a high affinity and a high relative specificity for TSH. Binding of TSH to these "receptors" is followed by a variety of biochemical events that lead to thyroid growth and increased function.

It now seems almost certain that the thyroid hyperfunction in Graves' disease results from the fact that, among the membrane-directed antibodies present in the blood of patients with this disorder, are some that are antibodies to the TSH receptor. These Graves'-specific antibodies bind to the thyroid cell membrane at the TSH receptor, and activate the gland in a manner analogous to the processes by which TSH does. This activity resides in the $F_{ab}$, not the $F_c$, portion of the molecule. Within this context, the presence of these TSH receptor-directed antibodies is what differentiates active Graves' disease, in which thyroid function is increased, from almost all patients with Hashimoto's disease and primary myxedema, in which thyroid function is normal or decreased.

At present, there are two major methods by which these "Graves'-specific" antibodies are detected. The first method involves the demonstration that the IgG isolated from the test serum are capable of inducing certain biochemical responses in human thyroid tissue in vitro. This test is not practical for widespread clinical application.

In the second method, the IgG are tested for their ability to inhibit the binding of $^{125}$I-labeled (bovine) TSH (TSH*) to the TSH receptor in the human thyroid cell membrane (TSH-binding inhibitory assay, TBI assay).

The latter method, commonly referred to by the names of its popularizers (Smith and Hall), is schematically represented in FIG. 1. ("Thyroid-Stimulating Immunoglobulins in Graves' Disease" The Lancet, Aug. 24, 1974 (Smith and Hall).) In practice, the Smith and Hall test is complicated by the fact that normal IgG also have an inhibitory effect on TSH* binding. This is probably due to the binding of normal IgG to the thyroid membrane, probably to $F_c$ receptors, resulting in hindrance to the binding of TSH*, as seen in FIG. 2. This non-specific inhibitory effect of normal IgG reduces the sensitivity of the test for detecting Graves' disease by creating overlap between values found with Graves' IgG and values found with normal IgG or Hashimoto's IgG. Not only in immunoassays for Graves'-specific antibodies, but in many immunoassays for other specific antibodies as well, false-positive responses occur due to interfering reactions by the reactive ends of similar antibodies.

Other methods have been suggested for detecting Graves'-specific IgG. For instance, Graves'-IgG (crude fractions) have been labeled with $^{125}$I and allowed to bind to thyroid membranes. ("Preparation of Radiolabeled Thyroid-Stimulating Immunoglobulins (TSI) by Recombining TSI Heavy Chains with $^{125}$I-Labeled Light Chains: Direct Evidence That the Product Binds to the Membrane Thyrotropin Receptor and Stimulates Adenylate Cyclase", *Endocrinology*, Vol. 103, No. 1 (Mehdi and Kriss); "Studies on a Receptor Assay for an Antibody to Human Thyroid Plasma Membrane", Acta Endocrinologica, 91 (1979) 89–98 (Ochi et al).) The ability of test IgG to inhibit the binding of the labeled IgG is then assessed. The problem with this method is that the results are not disease-specific. Hashimoto's-IgG, as well as Graves'IgG, inhibit the binding of the labeled IgG, owing to the fact that the crude labeled Graves'-IgG contains antibodies against other antigenic determinants in the thyroid membrane (e.g., antimicrosomal antibodies) that are common to Hashimoto's disease. Thus, the test assesses the presence in serum of both antimicrosomal antibodies and antibodies to the TSH receptor.

Since guinea pig fat cell membranes contain TSH receptors, akin to those present in the thyroid, another method that has been employed is to use 9guinea pig fat cell membranes in place of the human thyroid membranes in a standard Smith and Hall type assay. ("Interaction between Thyroid-Stimulating Immunoglobulins and Thyrotropin Receptors in Fat Cell Membranes", *Journal of Clinical Endocrinology and Metabolism*, Vol. 49 (Kishiuhara et al).) The advantage of the guinea pig fat cell membrane is that it does not contain determinants complementary to the antithyroid microsomal antibodies. Therefore, its antigens are more clearly disease-specific and interactions with the IgG of Hashimoto's disease are virtually eliminated. However, considerable inhibition of normal IgG remains a problem that reduces sensitivity of the assay.

In another method for detecting Graves'-specific antibodies, solubilized guinea pig fat cell membrane is used as a TSH-receptor. ("Adipocyte-TSH-Receptor-related Antibodies in Graves' Disease Detected by Immunoprecipitation", *Endocrinol. Japan*, April, 1982 (Konishi et al).) This fat cell membrane is incubated with labeled TSH and the test IgG. Graves'-IgG bind to some of the TSH receptors. An antihuman-IgG second antibody is used to precipitate the Graves'-IgG bound to the solubilized membrane. Labeled TSH bound to the precipitated membrane is counted. This method is shown schematically in FIG. 3.

There are two major weaknesses to this method. First, in binding to the TSH-receptor, Graves'-IgG doubtless inhibit some binding of labeled TSH, thus reducing the amount of indicator label in the final precipitate. Second, some binding of normal IgG to the membrane will occur. When the membranes are reacted with the second antibody, membranes to which both labeled TSH and normal IgG are bound will be precipitated, increasing the normal or blank value. Because of this non-specific interaction, the percentage of positive results obtained from samples of Graves' disease IgG by this method is lower than by the conventional Smith and Hall method.

Still another method used is to allow guinea pig fat cell membranes to interact with the test IgG, and them to add $^{125}$I-labeled Protein A. ("Membrane-Binding Antibodies in Patients with Graves' Disease and Other Autoimmune Diseases", *Journal of Clinical Endocrinology and Metabolism*, Vol. 55, No. 5 (Tao and Kriss).) The membranes are centrifuged down and counted. The problem with this method is that it yields high values with normal IgG, presumably because the protein A is binding to normal IgG bound non-specifically to the membrane. Whatever the cause, separation between Graves' and Hashimoto's diseases, and between Graves' disease and normals, is inadequate by this method. The same report describes the results of efforts to carry out a comparable assay, using whole serum rather than IgG fractions, but similar low sensitivity and non-specificity were observed.

Accordingly, it is a principal object of the present invention to develop an extremely sensitive immunoassay for Graves'-specific antibodies which would accurately separate patients with Graves' disease from normals and patients with other thyroid diseases.

It is another object of the present invention to provide such an immunoassay in which one step comprises occluding the $F_c$ ends of all of the IgG's in the system by interacting them with an anti-$F_c$ antibody.

It is a further object of the present invention to develop such an immunoassay that could be used successfully with whole serum, thus eliminating the costly and time-consuming need for the preparation of IgG fractions.

It is a still further object of the present invention to develop an immunoassay for a specific antibody in which interfering reactions by the reactive ends of similar antibodies are eliminated by the step of occluding the interfering reactive ends with an antibody against the interfering reactive ends.

SUMMARY OF THE INVENTION

The problems of the prior art are overcome by the instant invention which comprises an immunoassay for a specific antibody, particularly Graves'-specific antibody, in which interfering reactions by the reactive ends of similar antibodies are eliminated by the step of occluding the interfering reactive ends with an antibody against the interfering reactive ends.

The immunoassay for Graves'-specific antibodies in IgG fractions includes the steps of: (1) preparing an IgG fraction from test serum; (2) creating a solid phase system by interacting the test IgG fraction with an antibody against the $F_c$ fragment of human IgG; (3) radioactively labeling membranes containing thyroid-stimulating hormone receptors; (4) adding the labeled membranes to the solid phase system; (5) incubating the mixture; and (6) counting precipitated labeled membrane.

The immunoassay for Graves'-specific antibodies in whole serum includes the steps of: (1) coupling the antibody against the $F_c$ fragment of human IgG to a solid phase matrix, (2) incubating the test serum with the coupled, solid phase antibody; (3) radioactively labeling membranes containing thyroid-stimulating hormone receptors; (4) adding the labeled membranes to the solid phase system; (5) incubating the mixture; and (6) counting precipitated labeled membrane.

DESCRIPTION OF THE PREFERRED EMBODIMENTS

The first step in the immunoassay of Graves'-specific antibodies in preparations of IgG is to prepare an IgG fraction from a blood sample of a patient suspected of having Graves' disease. This IgG fraction may be obtained by any means known in the art, i.e., affinity chromotography.

Figure 1:
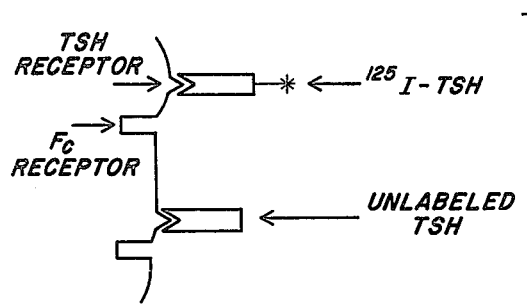
FIG. 1 is a schematic diagram of the Smith and Hall (prior art) TSH-binding inhibitory assay.
Figure 2:
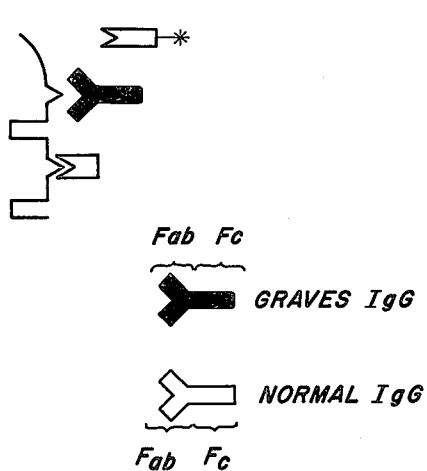
FIG. 2 is a schematic diagram showing non-specific inhibition of TSH binding by normal IgG in a Smith and Hall (prior art) TSH-binding inhibitory assay.
Figure 2:
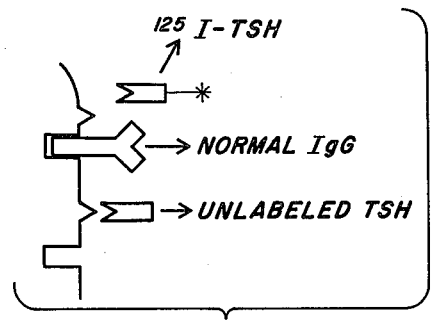
Figure 3:
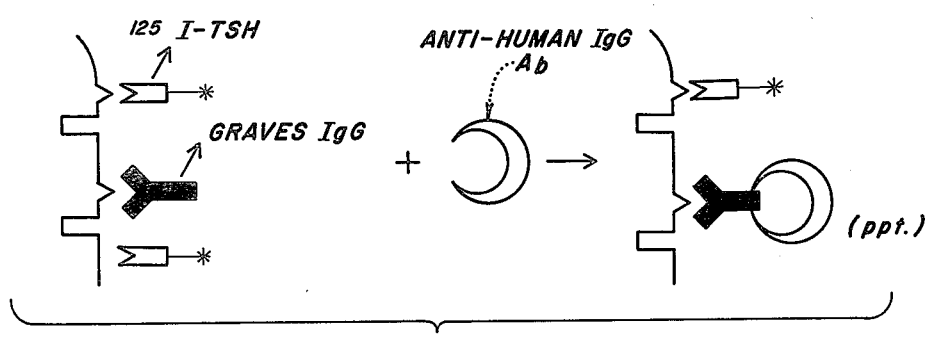
FIG. 3 is a schematic diagram of a prior art immunoassay for Graves'-specific antibodies.
Figure 4:
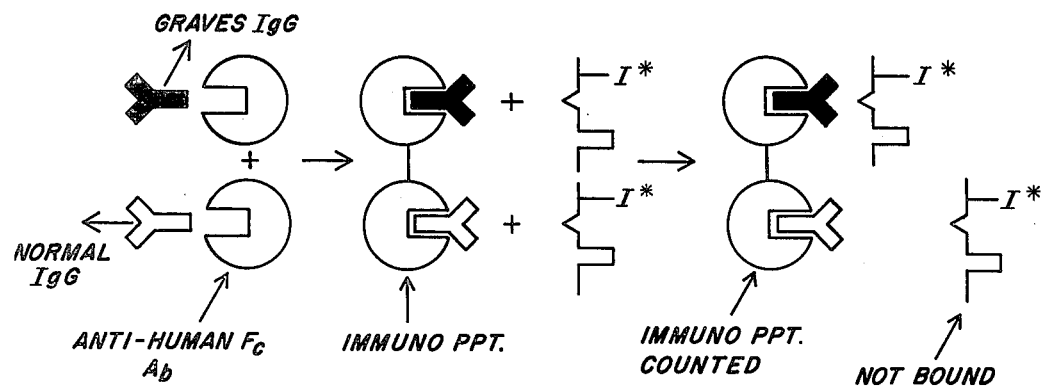
FIG. 4 is a schematic diagram of the immunoassay for Graves'-specific antibodies in IgG fractions, in accordance with the present invention.

As seen in FIG. 4, the next step is to interact the test IgG fraction with an antibody against the $F_c$ fragment of human IgG (anti-$F_c$ antibody). This is intended to occlude the $F_c$ end of all the IgG in this system, whether they be normal or Graves' IgG. Since the Fc ends of the IgG molecules are occluded by the anti-$F_c$ antibody, the non-disease-specific binding of normal IgG to the $F_c$ receptor is prevented. Use of the anti-$F_c$ antibody in this way greatly enhances the sensitivity and specificity of the test. The resulting immunoprecipitate creates a solid-phase system.

The first step in the immunoassay of Graves'-specific antibodies in whole serum is to couple an antibody against the $F_c$ fragment of human IgG to a solid phase matrix, such as Sepharose-4B beads. This can be accomplished with the aid of one of several coupling agents, such as cyanogen bromide.

Figure 5:
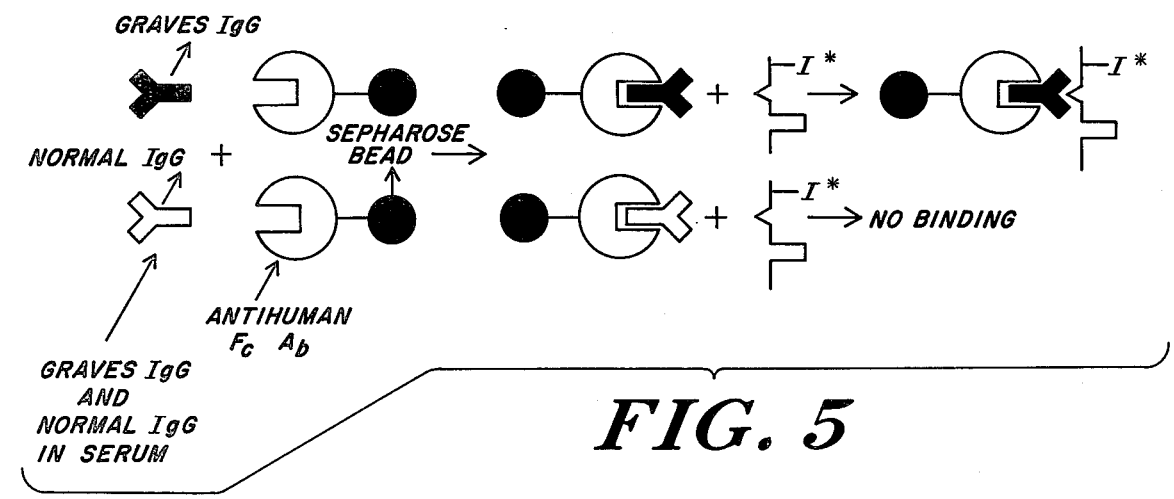
FIG. 5 is a schematic diagram of the immunoassay for Graves'-specific antibodies in whole serum, in accordance with the present invention.

As seen in FIG. 5, the next step is to interact the test serum specimen with the Sepharose-coupled anti-$F_c$ antibody. This is intended to occlude the $F_c$ end of all the test IgG in the test serum, whether they be normal IgG or Graves'-IgG. Since the $F_c$ ends of the IgG molecules are occluded by the anti-$F_c$ antibody, the non-disease-specific binding of normal IgG to the $F_c$ receptor is prevented. Use of the anti-$F_c$ antibody in this way greatly enhances the sensitivity and specificity of the test. The remaining steps are common to the assay of both IgG preparations and whole serum.

Radioactively labeled membranes containing TSH receptors are then added to the solid-phase system (IgG immunoprecipitate or sepharose beads) and the mixture is incubated. Any radioactive label may be used, but $^{125}$I is the preferred label. Although human thyroid membranes can be used in the immunoassay, the results would not be totally disease-specific, since crude Graves' IgG contains antibodies against other antigenic determinants in the thyroid membrane (e.g., antimicrosomal antibodies) that are common to Hashimoto's disease. The preferred membranes for the immunoassay are guinea pig fat cell membranes. The advantage of these membranes is that they do not contain determinants complimentary to the antithyroid microsomal antibodies. Therefore, the guinea pig fat cell membranes' antigens are more clearly disease-specific and interactions with the IgG of Hashimoto's disease are eliminated. After incubation of the mixture, precipitated labeled membrane is counted.

The present invention is further illustrated by the following non-limiting Examples.

EXAMPLE 1

Protocol for Assay Using IgG Fractions

Sample Preparation

An IgG fraction is prepared from the test serum. The protein concentration is measured and the sample diluted to a concentration of 1 mg/ml with 10 mM Tris-Hcl 0.5% Bovine Serum Albumin (BSA), pH 7.4. (Tris:-BSA)

Procedure (1) Place 50 ul aliquots of the IgG solutions in the microfuge tubes. Place 50 ul of Tris:BSA in "blank" tube.

(2) Add 50 ul of goat anti-human $F_c$ antiserum.

(3) Add 100 ul of Tris:BSA (4) Mix.

(5) Incubate for 4 hours at 4° C.

(6) Centrifuge the mixture in a Beckman Microfuge B for 5 minutes at 4° C.

(7) Aspirate the supernatant.

(8) Add $^{125}$I-labeled soluble fat cell membrane (SFCM) in 200 ul of Tris:BSA.

(9) Mix.

(10) Incubate for 1 hour at 22° C. in a shaking incubator.

(11) Centrifuge in a Beckman Microfuge B for 5 minutes at 4° C.

(12) After aspirating the supernatant, wash the pellet with 200 ul of Tris:BSA.

(13) Resediment in a Beckman Microfuge B.

(14) After aspirating the supernatant, count the pellet in gamma-counter.

Sample Results

Total $^{125}$I-labeled SFCM added: 30,000 cpm

| Counts in ppt: | |
|---|---|
| Graves-IgG | 1,800 cpm |
| Hashimoto's-IgG | 210 cpm |
| Normal-IgG | 220 cpm |
| Blank | 60 cpm |
| Calculations: | |
| Graves'-IgG: | 1800 − 60 = 1740 cpm |
| | 1740 × 100/30,000 = 5.80% |
| Hashimoto's IgG: | 210 − 60 = 150 cpm |
| | 150 × 100/30,000 = 0.50% |
| Normal-IgG: | 220 − 60 = 160 cpm |
| | 160 × 100/30,000 = 0.53% |

Figure 6:
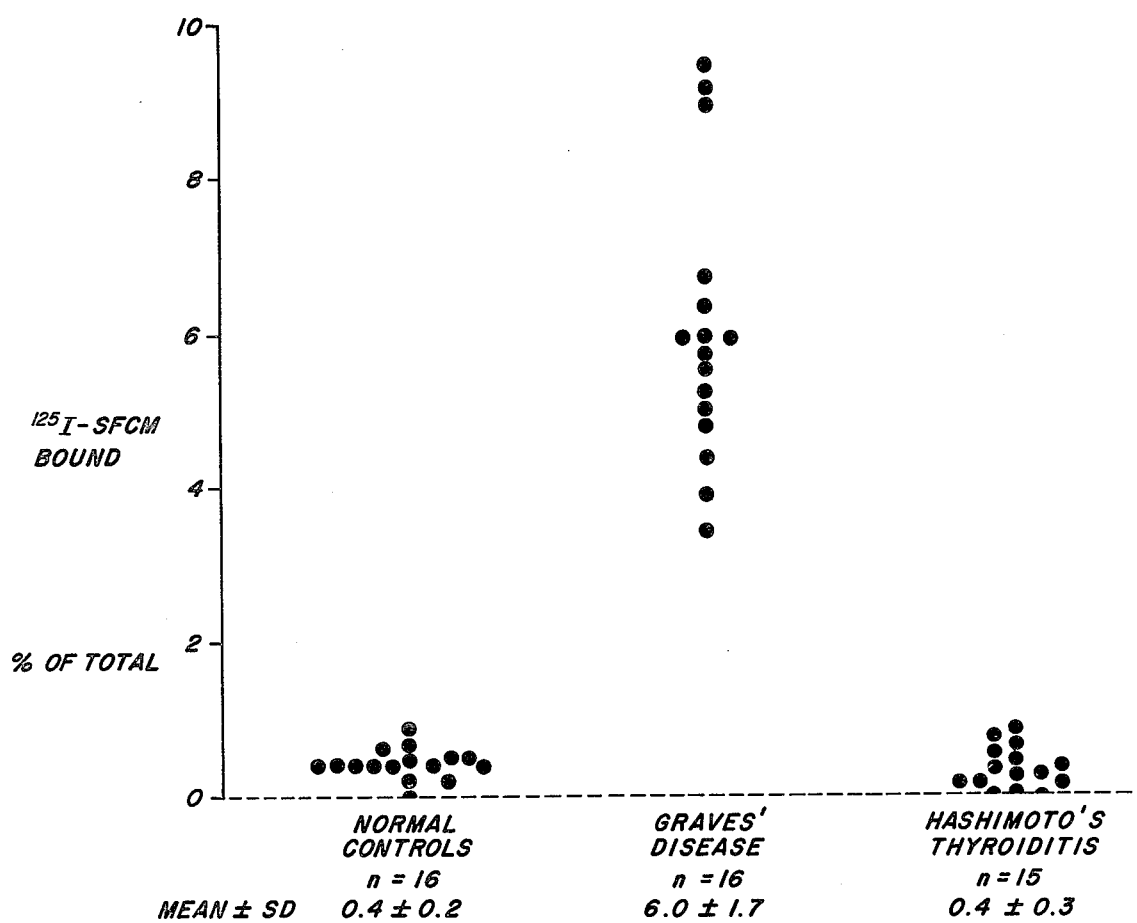
FIG. 6 is a graph showing test results in accordance with the present invention; and, FIG. 7 is a graph showing test results in accordance with the present invention.

The results of the assays of the IgG fractions of this example are shown in FIG. 6.

EXAMPLE 2

Protocol for Assay Using Whole Serum

Sample Preparation

Serum samples to be tested are diluted with 10 mM Tris-HCl, 0.5% BSA, pH 7.4 (Tris:BSA) to the ratio 1:1000.

Procedure (1) Place 100 ul of diluted serum samples in Microfuge tubes. Place 100 ul of buffer in "blank" tube.

(2) Add 50 ul of goat antibody to $F_c$ fragment of human IgG coupled to Cyanogen bromide (CN-Br) activated Sepharose 4B beads.

(3) Add 50 μl Tris:BSA.

(4) Mix.

(5) Incubate for 1 hour at 22° C.

(6) Centrifuge the mixture in a Beckman Microfuge B for 5 minutes at 4° C.

(7) After aspirating the supernatant, wash the beads with 200 ul of Tris:BSA.

(8) Resediment the mixture and aspirate the supernatant.

(9) Add $^{125}$I-labeled SFCM in 200 ul Tris:BSA (30,000 cpm).

(10) Mix.

(11) Incubate for 1 hour at 37° C. in a shaking incubator.

(12) Centrifuge the mixture in a Beckman Microfuge B for 5 minutes at 4° C.

(13) After aspirating the supernatant, wash the beads with 200 ul of Tris:BSA.

(14) Resediment the mixture and aspirate the supernatant.

(15) Count the beads in a gamma-counter.

Sample Results

Total $^{125}$I-labeled SFCM added: 25,000 cpm

| Counts in sediment: | |
|---|---|
| Graves'-IgG | 1,500 cpm |
| Normal-IgG | 600 cpm |
| Hashimoto's-IgG | 620 cpm |
| Blank: (IgG-free) | 620 cpm |
| Calculations: | |
| Graves'-IgG: | 1500 − 620 = 880 cpm |
| | 880 × 100/25,000 = 3.32% |
| Normal-IgG: | 600 − 620 = <0 |
| | <0/25,000 = <0% |
| Hashimoto's-IgG | 620 − 620 = 0 |
| | 0/25,000 = 0% |

Figure 7:
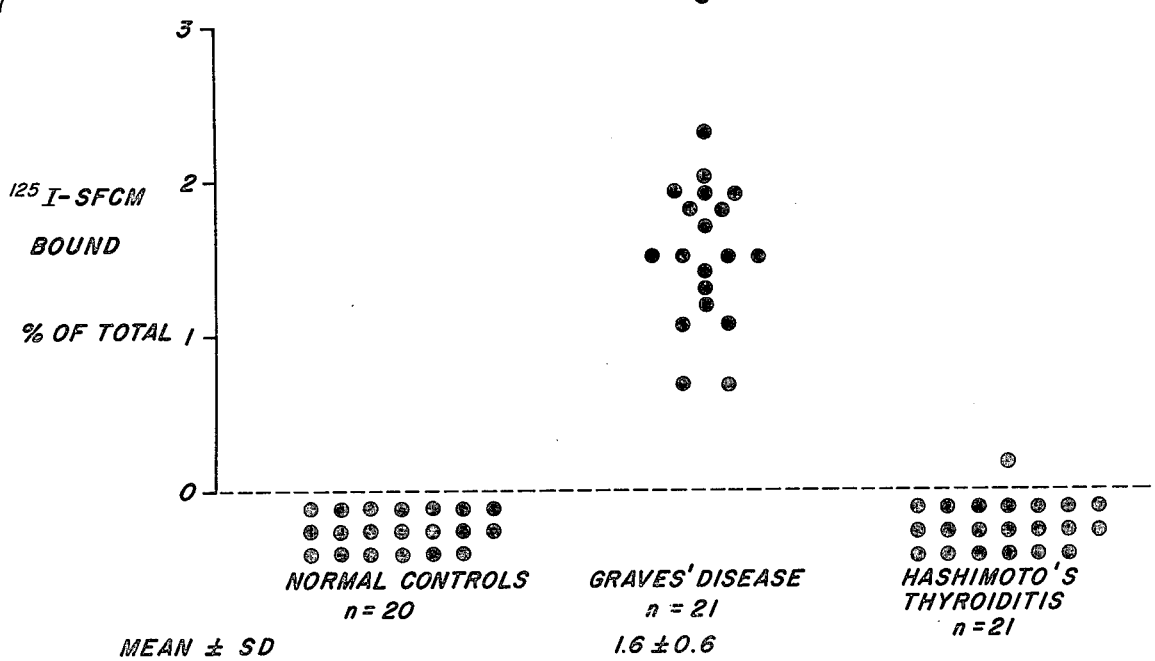

The results of the assays of whole serum of this example are shown in FIG. 7.

Although the invention has been described with reference to these preferred embodiments, other embodiments can achieve the same results. Variations and modifications of the present invention will be obvious to those skilled in the art and it is intended to cover in the appended claims all such modifications and equivalents.

I claim:

1. An immunoassay for Graves'-specific antibodies comprising the steps of:
    (a) preparing an IgG fraction from test serum;
    (b) creating a solid-phase system by interacting the test IgG fraction with an antibody against the $F_c$ fragment of human IgG;
    (c) radioactively labeling membranes containing thyroid-stimulating hormone receptors;
    (d) adding the labeled membranes to the solid-phase system;
    (e) incubating the mixture; and
    (f) counting precipitated labeled membrane.

2. An immunoassay for Graves'-specific antibodies comprising the steps of:
   (a) coupling an antibody against the $F_c$ fragment of human IgG to a solid phase matrix;
   (b) incubating whole test serum with the coupled, solid phase antibody;
   (c) radioactively labeling membranes containing thyroid-stimulating hormone receptors;
   (d) adding the labeled membranes to the solid-phase system;
   (e) incubating the mixture; and
   (f) counting precipitated label membrane.

3. The immunoassay of claims 1 or 2 wherein the membranes comprises human thyroid membranes.

4. The immunoassay of claims 1 or 2 wherein the membranes comprise guinea pig fat cell membranes.

5. The immunoassay of claims 1 or 2 wherein the membranes are labeled with $^{125}I$.

6. The immunoassay of claim 2 wherein in step a, a coupling agent is included.

7. The immunoassay of claim 6 wherein the coupling agent is cyanogen bromide.

8. In an immunoassay for a specific antibody in which similar antibodies have interfering reactive ends, the improvement which comprises occluding the interfering reactive ends of the similar antibodies.

9. The improvement of claim 8 wherein the interfering reactive ends are occluded by interacting the antibodies with an antibody against the interfering reactive end.

10. The assay of claim 9 wherein the reactive end is the $F_c$ region of the antibody.

11. In an immunoassay for a specific antibody in a mixture of antibodies, in which the antibody is measured by binding of said antibody to a labelled antigen, the improvement which comprises first occluding the non-antigen binding portions of the antibodies and then binding said specific antibody to said labelled antigen.

12. The improvement of claim 11 wherein said non-antigen binding portion of the antibody is the Fc region of the antibody.

13. The improvement of claim 11 wherein said specific antibody binds to said labelled antigen at the $F_{ab}$ region of the antibody.

* * * * *